(12) United States Patent
Tabibzadeh

(10) Patent No.: US 6,747,004 B1
(45) Date of Patent: Jun. 8, 2004

(54) METHOD FOR INDUCING GROWTH AND ENHANCING SURVIVAL OF NERVOUS TISSUE

(75) Inventor: Siamak Tabibzadeh, Albertson, NY (US)

(73) Assignee: North Shore - Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/561,861

(22) Filed: Apr. 28, 2000

Related U.S. Application Data

(63) Continuation-in-part of application No. 09/302,094, filed on Apr. 29, 1999, now abandoned.

(51) Int. Cl.[7] .................. A61K 38/00; A01N 61/00; A01N 37/18; C12N 5/00
(52) U.S. Cl. ................... 514/12; 514/1; 514/2; 514/44; 435/375
(58) Field of Search ............... 514/2, 1, 12, 44; 435/375; 530/350

(56) References Cited

PUBLICATIONS

Barinaga M., 1994, Science, 264, pp. 772–774.*
Jackowski, A. 1995, Br.J. of Neurosurgery, 9, pp. 303–317.*

\* cited by examiner

Primary Examiner—John Ulm
Assistant Examiner—Olga N. Chernyshev
(74) Attorney, Agent, or Firm—Amster, Rothstein & Ebenstein LLP

(57) ABSTRACT

The present invention provides a method of inducing growth or enhancing survival of nervous tissue comprising contacting the nervous tissue with an amount of ebaf effective to induce the growth or enhance the survival of the nervous tissue. The present invention also provides a method for treating a subject having damaged or degenerated nervous tissue comprising administering to the subject an amount of ebaf effective to treat the damaged or degenerated nervous tissue in the subject. The present invention further provides a method for treating a neurodegenerative disease in a subject comprising administering an amount of ebaf effective to treat the neurodegenerative disease. The present invention still further provides a method for preventing the onset or reducing the severity of damaged or degenerated nervous tissue in a subject comprising administering an amount of ebaf effective to prevent the onset or reduce the severity of the damaged or degenerated nervous tissue. Finally, the present invention provides a method for inducing growth or enhancing survival of nervous tissue comprising contacting the nervous tissue with a modulator of ebaf expression in an amount effective to induce or enhance expression of ebaf and induce the growth or enhance the survival of the nervous tissue.

9 Claims, 5 Drawing Sheets

Figure 2 cDNA sequence of ebaf

```
AAT TCG GCA CGA GCC CCA CTC TGC CTC CTG CTC CCC CAG GGC AGC ACC ATG TGG CCC CTG
TGG CTC TGC TGG GCA CTC TGG GTG CTG CCC CTG GCT GGC CCC GGG GCG GCC CTG ACC GAG
GAG CAG CTC CTG GGC AGC CTG CTG CGG CAG CTG CAG CTC AGC GAG GTG CCC GTA CTG GAC
AGG GCC GAC ATG GAG AAG CTG GTC ATC CCC GCC CAC GTG AGG GCC CAG TAT GTA GTC CTG
CTG CGG CGC AGC CAC GGG GAC CGC TCC CGC GGA AAG AGG TTC AGC CAG AGC TTC CGA GAG
GTG GCC GGC AGG TTC CTG GCG TCG GAG GCC AGC ACA CAC CTG CTG GTG TTC GGC ATG GAG
CAG CGG CTG CCG CCC AAC AGC GAG CTG GTG CAG GCC GTG CTG CGG CTC TTC CAG GAG CCG
GTC CCC AAG GCC GCG CTG CAC AGG CAC GGG CGG CTG TCC CCG CGC AGC GCC CAG GCC CGG
GTG ACC GTC GAG TGG CTG CGC GTC CGC GAC GAC GGC TCC AAC CGC ACC TCC CTC ATC GAC
TCC AGG CTG GTG TCC GTC CAC GAG AGC GGC TGG AAG GCC TTC GAC GTG ACC GAG GCC GTG
AAC TTC TGG CAG CAG CTG AGC CGG CCC CGG CAG CCG CTG CTG CTA CAG GTG TCG GTG CAG
AGG GAG CAT CTG GGC CCG CTG GCG TCC GGC GCC CAC AAG CTG GTC CGC TTT GCC TCG CAG
GGG GCG CCA GCC GGG CTT GGG GAG CCC CAG CTG GAG CTG CAC ACC CTG GAC CTC AGG GAC
TAT GGA GCT CAG GGC GAC TGT GAC CCT GAA GCA CCA ATG ACC GAG GGC ACC CGC TGC TGC
CGC CAG GAG ATG TAC ATT GAC CTG CAG GGG ATG AAG TGG GCC AAG AAC TGG GTG CTG GAG
CCC CCG GGC TTC CTG GCT TAC GAG TGT GTG GGC ACC TGC CAG CAG CCC CGG GAG GCC CTG
GCC TTC AAT TGG CCA TTT CTG GGG CCG CGA CAG TGT ATC GCC TCG GAG ACT GCC TCG CTG
CCC ATG ATC GTC AGC ATC AAG GAG GGA GGC AGG ACC AGG CCC CAG GTG GTC AGC CTG CCC
AAC ATG AGG GTG CAG AAG TGC AGC TGT GCC TCG GAT GGG GCG CTC GTG CCA AGG AGG CTC
CAG CCA TAG GCG CCT GGT GTA TCC ATT GAG CCC TCT AAC TGA ACG TGT GCA TAG AGG TGG
TCT TAA TGT AGG TCT TAA CTT TAT ACT TAG CAA GTT ACT CCA TCC CAA TTT AGT GCT CCT
GTG TGA CCT TCG CCC TGT GTC CTT CCA TTT CCT GTC TTT CCC GTC CAT CAC CCA TCC TAA
GCA CTT ACG TGA GTA AAT AAT GCA GCT CAG ATG CTG AGC TCT AGT AGG AAA TGC TGG CAT
GCT GAT TAC AAG ATA CAG CTG AGC AAT GCA CAC ATT TTC AGC TGG GAG TTT CTG TTC TCT
GGC AAA TTC TTC ACT GAG TCT GGA ACA ATA ATA CCC TAT GAT TAG AAC TGG GGA AAC AGA
ACT GAA TTG CTG TGT TAT ATG AGG AAT TAA AAC CTT CAA ATC TCT ATT TCC CCC AAA TAC
TGA CCC ATT CTG GAC TTT TGT AAA CAT ACC TAG GCC CCT GTT CCC CTG AGA GGG TGC TAA
GAG GAA GGA TGA AGG GCT TCA GGC TGG GGG CAG TGG ACA GGG AAT TGG GAT ACC TGG ATT
CTG GTT CTG ACA GGG CCA CAA GCT AGG ATC TCT AAC AAA CGC AGA AGG CTT TGG CTC GTC
ATT TCC TCT AAA AGA GGA GCT GGG CTT CAG CTC TAA GAA CTT CAT TGC CCT GGG GAT
CAG ACA GCC CCT ACC TAC CCC TGC CCA CTC CTC TGG AGA CTG AGC CTT GCC CGT GCA TAT
TTA GGT CAT TTC CCA CAC TGT CTT AGA GAA CTT GTC ACC AGA AAC CAC ATG TAT TTG CAT
GTT TTT TGT TAA TTT AGC TAA AGC AAT TGA ATG TAG ATA CTC AGA AGA AAT AAA AAA TGA
TGT TTC AAA AAA AAA AAA AAA AAC TCG AG
```

Protein sequence of ebaf

```
MWPLWLCWALWVLPLAGPGAALTEEQLLGSLLRQLQLSEVPVLDRADMEKLVIPAHVRAQYVVLLRRSHGDRSRGKRFSQ
SFREVAGRFLASEASTHLLVFGMEQRLPPNSELVQAVLRLFQEPVPKAALHRHGRLSPRSAQARVTVEWLRVRDDGSNRT
SLIDSRLVSVHESGWKAFDVTEAVNFWQQLSRPRQPLLLQVSVQREHLGPLASGAHKLVRFASQGAPAGLGEPQLELHTL
DLRDYGAQGDCDPEAPMTEGTRCCRQEMYIDLQGMKWAKNWVLEPPGFLAYECVGTCQQPPEALAFNWPFLGPRQCIASE
TASLPMIVSIKEGGRTRPQVVSLPNMRVQKCSCASDGALVPRRLQP
```

METHOD FOR INDUCING GROWTH AND ENHANCING SURVIVAL OF NERVOUS TISSUE

CROSS-REFERENCE TO RELATED APPLICATION

This is a continuation-in-part of co-pending application Ser. No. 9/302,094, filed Apr. 29, 1999 now abandoned, the content of which is hereby incorporated by reference in its entirety.

STATEMENT OF GOVERNMENT INTEREST

This invention was made with government support under NIH Grant No. CA46866. As such, the U.S. government has certain rights in this invention.

BACKGROUND OF THE INVENTION

Death or destruction of nervous tissue such as neurons or glial cells is associated with a variety of degenerative disorders of the nervous system. These disorders include, for example, degenerative diseases such as Alzheimer's disease, Parkinson's disease, Huntington's chorea, and amyotrophic lateral sclerosis. Necrosis or loss of neurons is also associated with neuropathies of the central, peripheral or motor neurons as a result of disease states such as diabetes. In addition, damage to neurons may result from ischemia due to stroke, trauma (e.g. burns and wounds), kidney dysfunction as well as the toxic effects of drugs used to treat cancer and AIDS. Further, the loss of neurons may result in dementia associated with aging.

Currently, there are no known effective treatments for damaged or degenerated nervous tissue. Certain growth factors such as ciliary neurotrophic factor (CNTF) have been proposed for the treatment of neurodegenerative diseases such as Alzheimer's disease. However, the use of CNTF has not been successful in clinical trials. Thus, there is a present need for the identification of new agents for treating damaged and degenerated nervous tissue.

Kothapalli, et al. described the identification of a novel human gene encoding endometrial bleeding associated factor protein ("ebaf") that is associated with abnormal endometrial bleeding (*J. Clin. Invest.*, 99(10):2342–50, 1997). The ebaf gene is located on human chromosome 1 at band q42.1, and the nucleotide and deduced amino acid sequences are known (Kothapalli, et al., 1997). The sequence of the ebaf protein also shows homology and structural features of the members of the TGF-β superfamily (Kothapalli, et al., 1997). The ebaf gene is expressed in human endometrium in the late secretory and menstrual phases and absent in the early and mid-secretory endometria (Tabibzadeh, et aL, *Mol. Hum. Reprod*, 4(6):595–602, 1998), and also in certain adenocarcinomas that exhibited mucinous differentiation including colonic, duodenal, and ovarian carcinomas (Tabibzadeh, et al., *Front. Biosci.*, 15(2):18–25, 1997).

Meno, et al. have described two mouse members of the TGF-β superfamily, designated Lefty-1 and Lefty-2. These are expressed in a left-right asymmetric fashion in mouse embryos, and are separated by about 30 kb on mouse chromosome 1H2 (Meno, et al., *Genes Cells*, 2(8):513–24, 1997). Meno, et al. also reported that Lefty-1 induces NCAM-1 (a neural marker) in the absence of mesoderm induction, and hypothesized that the direct neutralizing activities of Lefty-1, similar to BMP antagonists such as noggin and chordin, may antagonize BMP (bone morphogenic protein)-mediated signals in tissues positioned on the left side of mouse embryos.

Recently, Kosaki, et al. described the identification of two human lefty genes, designated Lefty-A and Lefty-B, that are separated by approximately 50 kb on chromosome 1q42 (*Am. J. Hum. Genet.* 64(3):712–21, 1999). Lefty-A was described as being identical to ebaf. Although human Lefty-A and Lefty-B and mouse Lefty-1 and Lefty-2 are similar, Kosaki, et al. described that human Lefty-A and Lefty-B are more similar to each other than to mouse Lefty-1 and Lefty-2. In this regard, Kosaki, et al. described that Lefty-A and Lefty-B are 96% homologous and mouse Lefty-1 and Lefty-2 are 90% homologous, while the cross-species homology is only 81–82%. Thus, Kosaki, et al. suggested that sequence analysis alone precludes determination of specific orthologous relationships (i.e. whether Lefty-A is the functional equivalent of Lefty-1).

SUMMARY OF THE INVENTION

The present invention is based on the discovery that ebaf is associated with the development and growth of nervous tissue. Based on this finding, the present invention provides a method for inducing the growth or enhancing survival of nervous tissue comprising contacting the nervous tissue with an amount of ebaf effective to induce the growth or enhance the survival of the nervous tissue. The present invention also provides a method for treating a subject having damaged or degenerated nervous tissue comprising administering to the subject an amount of ebaf effective to treat the damaged or degenerated nervous tissue.

The present invention further provides a method for treating a neurodegenerative disease in a subject comprising administering an amount of ebaf effective to treat the neurodegenerative disease. The present invention still further provides a method for preventing the onset or reducing the severity of damaged or degenerated nervous tissue in a subject comprising administering an amount of ebaf effective to prevent the onset or reduce the severity of the damaged or degenerated nervous tissue.

Lastly, the present invention provides a method for inducing growth or enhancing survival of nervous tissue comprising contacting the nervous tissue with a modulator of ebaf expression in an amount effective to induce or enhance expression of ebaf and induce the growth or enhance the survival of the nervous tissue. Additional objects of the present invention will be apparent in view of the description which follows.

BRIEF DESCRIPTION OF THE DRAWINGS

FIG. 1A=actin (mesoderm marker); FIG. 1B=XAG1 (cement gland marker); FIG. 1C=H8 (endodermal marker); FIG. 1D=ctokeratin (epithelial marker); FIG. 1E=globin (ventral mesoderm); FIG. 1F=X1hbox9 (spinal cord marker); FIG. 1G=NRP-1 (general marker); FIG. 1H=EN2 (mid-hind brain marker); FIG. 1I=OTXA (forebrain marker); FIG. 1J=KROX20 (hindbrain marker); FIG. 1K=EF1 α (housekeeping gene). FIGS. 1A–1D: Lane 1: whole embryo RNA used as control.

Lane 2: uninjected with ebaf RNA. Lane 3: injected with 20 pg of ebaf RNA. Lane 4: injected with 200 pg of ebaf RNA. Lane 5: injected with injected with 2 ng of ebaf RNA. FIGS. 1E–1K: Lane 1: whole embryo RNA used as control. Lane 2: RT-PCR control in which the reverse transcriptase was omitted from the RT reaction. Lane 3: uninjected with the ebaf RNA. Lane 4: injected with 20 pg of ebaf RNA; Lane 5: injected with 200 pg of ebaf RNA. Lane 6: injected with 2 ng of ebaf RNA.

FIG. 2 depicts the nucleotide sequence (SEQ ID NO: 1) and corresponding amino acid sequence (SEQ ID NO: 2) for ebaf.

DETAILED DESCRIPTION OF THE INVENTION

Figures 1A, 1B, 1C, 1D, 1E, 1F, 1G, 1H, 1I, 1J, 1K:
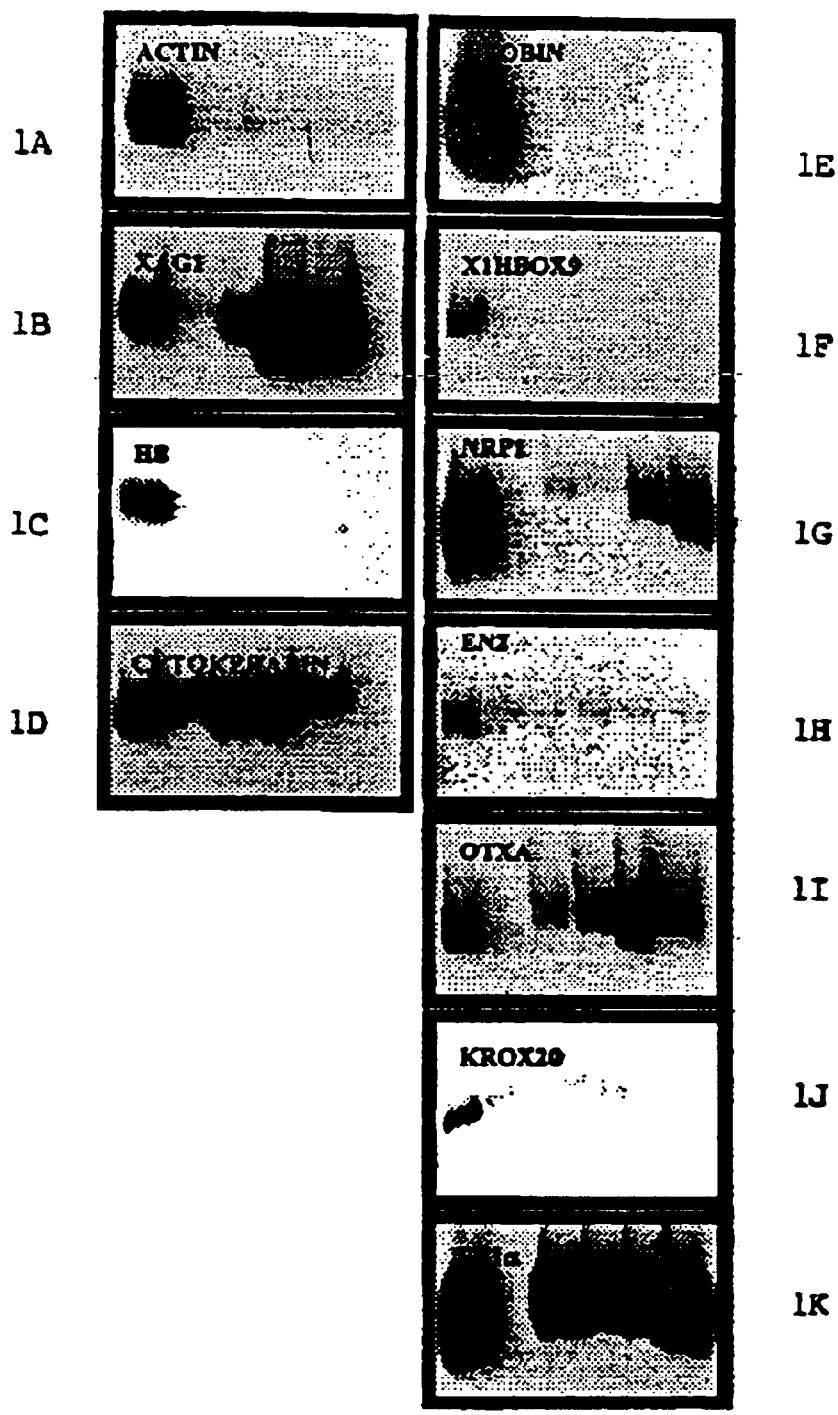
FIGS. 1A–1K demonstrate the effect of ebaf on the gene transcription in the development of the various tissue markers in the blastocyst of the Xenopus laevis. The ebaf RNA was prepared by in vitro transcription and was injected into the two cell stage Xenopus laevis blastocyst as described in the example. The animal caps were removed at 24 hours and the RNA was reverse transcribed and then cDNA was subjected to PCR using primers to the Xenopus laevis mRNA as shown.

The present invention provides a method for inducing growth or enhancing survival of nervous tissue that comprises contacting the nervous tissue with an amount of ebaf effective to induce the growth or enhance the survival of the nervous tissue. The method of the present invention may be used in the culturing of nervous tissue in vitro and also for the inducing growth and enhancing survival of nervous tissue in vivo.

As used herein, "nervous tissue" includes the neurons and neuroglia. "Neurons" are any of the conducting or nerve cells of the nervous system that typically consist of a cell body containing the nucleus and surrounding cytoplasm (perikaryon), several short radiating processes (dendrites), and one long process (the axon), which terminates in twig-like branches (telodendrons) and may have branches (collaterals) projecting along its course. "Neuroglia" are the neuroglial cells or glial cells which form the supporting structure of the nervous tissue. "Nervous tissue" includes the nervous tissue present in both the central nervous system and the peripheral nervous system.

As used herein, "growth" is an increase in thickness, diameter, length, mass and/or number of one or more of the components of the nervous tissue including but not limited to the perikaryon, the neurofibril, the nissl bodies, the axon, the dentrites, the telodenria, the myelin sheath, the neurilemma, the schwann cells, and/or the neuroglial or glial cells, and includes the generation or regeneration of one or more of the components of the nervous tissue. "Enhance the survival" of the nervous tissue is the full or partial protection of the nervous tissue from further death, degeneration, damage or injury.

With respect to the culturing of nervous tissue in vitro, it is believed that the ability of ebaf to induce the growth or enhance the survival of nervous tissue renders ebaf particularly useful for culturing nervous tissue in vitro. In this connection, ebaf may be introduced into the culture media by adding the ebaf protein directly to the culture media or by introducing nucleic acid encoding ebaf to the nervous tissue or other cells in a manner permitting expression of ebaf in amounts sufficient to induce the growth or enhance the survival of the nervous tissue. The culturing of nervous tissue in vitro may be desirable for preparing nervous tissue for transplantation, diagnostics, drug screening, and the like.

Concerning in vivo treatment, the ability of ebaf to induce the growth or enhance the survival of nervous tissue renders ebaf particularly useful for treating damaged or degenerated nervous tissue in a subject. The subject is preferably a mammal (e.g. humans, domestic animals, commercial animals), and most preferably a human. The damaged or degenerated nervous tissue may be associated with a neurodegenerative disease such as Alzheimer's disease, Parkinson's disease, Huntington's chorea, amyotrophic lateral sclerosis, dementia, or Pick's disease, congenital hydrocephalus, and the like. It is also within the confines of the present invention that the damaged or degenerated nervous tissue may result from an injury associated with trauma, cerebral hemorrhage, aneurysms, hypertensive encephalopathy, subarachanoid hemorrhage, diabetes, kidney dysfunction, ischemia, the treatment of therapeutic agents such as chemotherapy agents and antiviral agents, and other diseases or conditions prone to result in damaged or degenerated nervous tissue.

Thus, by treating the damaged or degenerated nervous tissue, it is believed that ebaf is useful for the treatment of neurodegenerative diseases. Similarly, by treating damaged or degenerated nervous tissue resulting from injury associated with trauma, cerebral hemorrhage, aneurysms, hypertensive encephalopathy, subarachanoid hemorrhage, diabetes, kidney dysfunction, ischemia, the treatment of therapeutic agents such as chemotherapy agents and antiviral agents, and other diseases or conditions prone to result in damaged or degenerated nervous tissue, it is believed that ebaf would be effective either alone or in combination with therapeutic agents used in the treatment of these diseases, conditions or disorders.

Furthermore, the ability of ebaf to induce the growth or enhance the survival of nervous tissue renders ebaf useful for preventing the onset or reducing the severity of damaged or degenerated nervous tissue. For example, a subject recently diagnosed with a neurodegenerative disease or predisposed to having a neurodegenerative disease based on family history may be considered a candidate for ebaf treatment. Similarly, it is envisioned that ebaf may be used in treating patients with diabetes, cancer or AIDS to prevent the onset or reduce the severity of damage or degenerative nervous tissue resulting from the disease or drugs used to treat these diseases or conditions.

In addition, since ebaf induces the growth or enhance the survival of nervous tissue, ebaf may be useful for enhancing wound healing, organ regeneration, organ transplantation (e.g., heart, kidney, lung, and liver), the transplantation of artificial organs, and in the acceptance of grafts (e.g skin, appendages, etc.).

In accordance with the methods of the present invention, the contacting or administration of ebaf may be effected by introduction or administration of the ebaf protein itself, or by the introduction or administration of a nucleic acid encoding ebaf in a manner permitting expression of the ebaf protein. The ebaf protein may be produced synthetically or recombinantly, or may be isolated from native cells, but is preferably recombinantly produced using the cDNA encoding ebaf (as set forth in FIG. 2) and conventional techniques. As used herein, the ebaf protein has the amino acid sequence set forth in FIG. 2. However, it is within the confines of the present invention that the protein includes functional variants thereof (i.e. proteins having ebaf protein activity) that are preferably 90% or greater in homology. In addition, the present invention also includes fragments of the ebaf protein with biological activity (i.e. peptide fragments that induce growth and/or enhance survival of neurons) and related peptide analogues thereof that exert similar biological activity. The ebaf protein may be administered to a tissue or subject by known techniques for the administration of proteins such as, for example, by injection or transfusion. When the damaged or degenerated nervous tissue is localized to a particular portion of the body, such as the brain, it may be desirable to administer the protein directly to the nervous tissue by injection or some other means (such as introducing ebaf into the cerebrospinal fluid or the blood). The amount of ebaf protein is an amount effective to promote the growth or enhance the survival of the nervous tissue, and is readily determinable to the skilled artisan.

ebaf also may be administered by introducing the nucleic acid encoding ebaf into a sufficient number of the cells of the nervous tissue (such as neurons, glial cells or Schwann cells, for example) in a manner permitting expression of ebaf in sufficient quantities to treat the damaged or degenerated nervous tissue. The nucleic acid may be introduced using conventional procedures known in the art including but not limited to electroporation, DEAE Dextran, monocationic liposome fusion, polycationic liposome fusion, protoplast fusion, DNA coated microprojectile bombardment, by creation of an in vivo electrical field, injection with recombinant replication-defective viruses, homologous recombination, naked DNA transfer, gene therapy, viral vectors, expression vectors, or a combination thereof. Recombinant viral vectors suitable for gene therapy include but are not limited to vectors derived from the genomes of viruses such as HSV, adenovirus, adeno-associated virus, Semiliki Forest virus, cytomegalovirus and vaccinia virus. It also is within the confines of the present invention that the nucleic acid encoding ebaf may be introduced into suitable cells in vitro (e.g. Schwann cell or glial cells) using conventional procedures. The cells expressing ebaf may then be administered to the subject to treat the damaged or degenerated nervous tissue. To reduce rejection, the cells are preferably removed from the patient, subjected to the DNA techniques to incorporate the nucleic acid encoding ebaf, and then reintroduced into the patient.

Depending upon the desired use of ebaf, it is within the confines of the invention that ebaf may be used alone or in combination with one or more therapeutic agents such as growth factors to treat the damaged or degenerated nervous tissue. In addition, ebaf may be used in combination with other therapeutic agents such as chemotherapeutic agents or antiviral agents.

Finally, the present invention provides a method for inducing growth or enhancing survival of nervous tissue comprising contacting the nervous tissue with a modulator of ebaf expression in an amount effective to induce or enhance expression of ebaf and induce the growth or enhance the survival of the nervous tissue. Examples of modulators of ebaf expression include but are not limited to retinoic acid, estrogen or progesterone. It is also within the confines of the present invention that the modulators of ebaf expression may be used for both in vitro and in vivo applications as discussed above, including, for example, the treatment of damaged or degenerated nervous tissue, the treatment of neurodegenerative diseases, for preventing the onset or reducing the severity of damaged or degenerated nervous tissue, and the like.

The present invention is described in the following examples which are set forth to aid in the understanding of the invention, and should not be construed to limit in any way the scope of the invention as defined in the claims which follow thereafter.

EXAMPLE 1 ebaf RNA was injected into two cell stage blastocysts of the Xenopus laevis. The RNA was injected in various doses to show a dose response effect. The blastocysts were allowed to grow in vitro for several hours and then the animal caps were dissected away and further maintained in vitro until removed. Blastocysts that did not receive the ebaf RNA and the whole embryo served as controls. The RNAs were extracted from the injected, uninjected animal caps and the whole embryos which served as a positive control. These RNAs were reverse transcribed into cDNA and then amplified by PCR using various primer sets against markers of different tissues. The findings demonstrate that while ebaf has no effect on the development of endoderm and the mesoderm layers, ebaf inhibited the epidermization and enhanced the development of neuronal markers (see FIG. 1). ebaf also induced the neural marker NCAM (not shown). These tests also demonstrate that ebaf does not enhance the development of the spinal cord or hindbrain, rather its effect is precisely confined to the development of the forebrain (FIG. 1). In addition, morphologically, the brains of the frogs with ebaf induction were larger than the controls (not shown).

The activity of the ebaf is remarkably similar to those elicited by BMP antagonists such as noggin, chordin and follistatin (Weinstein D, et aL, Neural inducation in the frog Xenopus laevis. In: Inhibin, activin and follistatin. Serono Symposia USA, Norwell, Mass. Eds: Aono T, Sugino H, and Vale WW. A Serono Symposia SA Publication. Springer-Verlag, N.Y., 214–219, 1997). These proteins bind directly to ligands and block their binding to the receptors. In view of the lack of the cysteine residue required for dimerization of the members of the TGF-beta family (Kothapalli, et al., 1997), ebaf is likely not to form dimers and may bind to the receptor of the TGF-beta family members rather than to the ligand. By virtue of this binding, ebaf may inhibit the activity of one or several members of the TGF-beta superfamily.

The biological effects of the members of the TGF-beta family are signaled through two classes of molecules designated as type I and type II receptors. These are transmembrane serine-threonine kinases that share homology with each other but have distinctive features. The dimerized ligand first binds the type II receptor and the type I receptor is subsequently recruited leading to the formation of a heteromeric complex. Within this complex, the type II receptor which is constitutionally active, phosphorylates the type I receptor in the GS (glycine-serine rich) domain. In the case of BMP and activin, the ligand first binds to the type I receptor (Padgett, et al, Bioessays, 20(5):382–90, 1998). The ebaf monomers may bind to the receptor of the TGF-beta family members and may prevent their activity.

EXAMPLE 2

The following experiments were done in vitro to assess the neurogenic potential of ebaf. First, the mitogenic effect of ebaf on the cells isolated from rat embryo forebrain was determined. Then, whether ebaf increases the number of neurons in such cultures was determined. Based on the findings presented below, it is concluded that ebaf increases proliferation of forebrain cells and increases their maturation to neuronal cells.

Effect of Ebaf on Proliferation of Rat Embryo Forebrain Cells in Culture.

Figure 3:
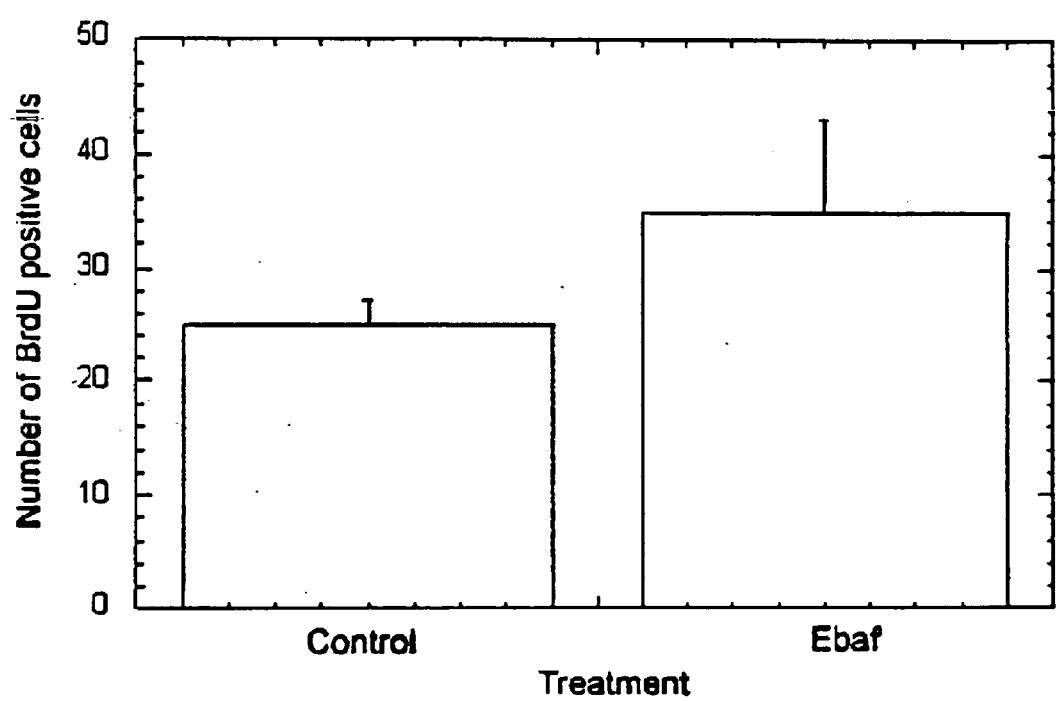
FIG. 3 depicts the effect of ebaf on proliferation of rat embryo forebrain cells. Cultures of 16 day old (E16) rat embryonic forebrain cells were incubated with supernatants of cells producing ebaf and the control cultures received DMEM medium alone in presence of BrdU for one day, followed by staining for BrdU. Bars represent mean BrdU+ cell counts±standard errors of the mean (SEM).

Cultures of dissociated, embryonic, day 16 (E16), rat forebrain were established in 24-well tissue culture plates with equal number ($250\times10^3$/well) of cells. These were maintained overnight in a chemically defined medium. Next morning, the experimental culture wells received overnight culture supernatant of confluent ebaf transfected cells collected in DMEM medium. The control culture wells received DMEM medium alone. Bromodeoxyuridine (BrdU) was added to all culture vessels (1 μl of a 1 mM solution per ml). The next day, these cultures were stained for BrdU. The experiment was done in triplicate. Results are shown in FIG. 3.

Effect of Ebaf on Neuronal Number in Rat Embryo Forebrain Cell Cultures.

Figure 4:
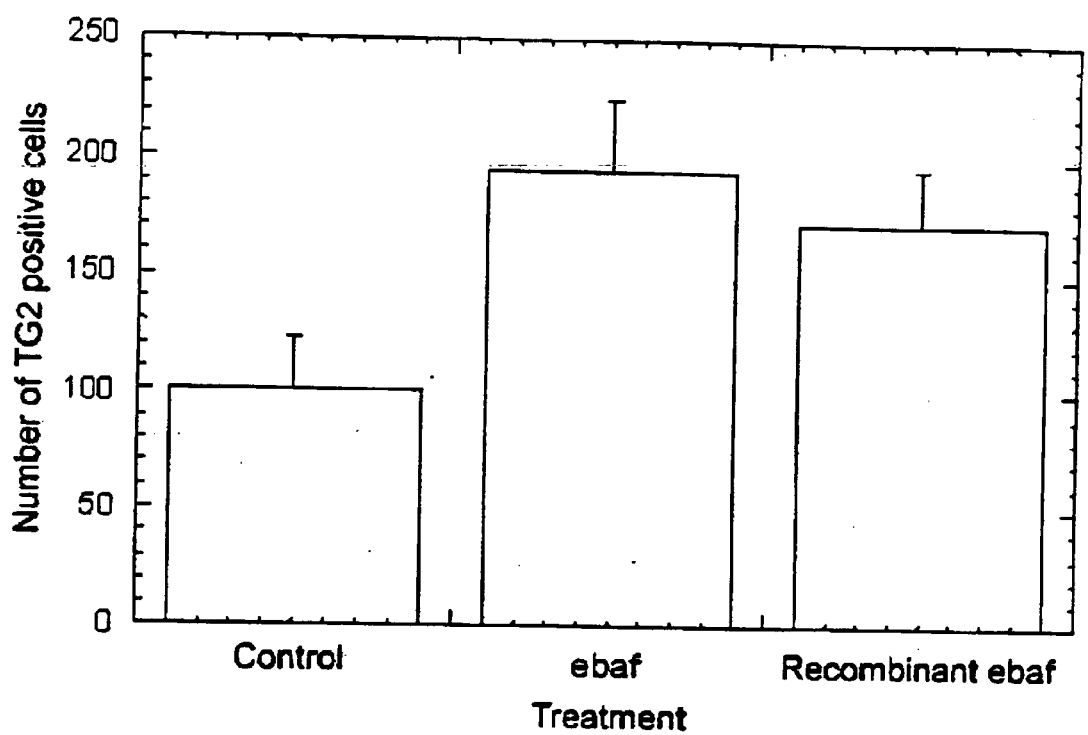
FIG. 4 depicts the effect of ebaf on number of TG-2 positive rat embryo forebrain cells. Cultures of 16 day (E16) old rat embryonic forebrain cells were incubated with supernatants of cells producing ebaf, recombinant ebaf (5 ng/ml) and the DMEM medium alone. After 9 days in culture, these were stained with TG-2 antibody. Bars represent mean TG2+ cells±standard errors of the mean (SEM) on repeated measurements.

Cultures of dissociated, embryonic, day 16 (E16), rat forebrain were established in 24-well tissue culture plates with equal number ($250\times10^3$/well) of cells. These were maintained overnight in a chemically defined medium. Next morning, the experimental culture wells received overnight culture supernatant of confluent ebaf transfected cells collected in DMEM medium. Other cultures received a recombinant E coli ebaf (26 kD) at 5 ng/ml. The control culture wells received DMEM medium alone. These were incubated for nine days without changing the medium. After nine days of culturing, cells stained with TG-2 antibody which marks the neurons (TG-2: Honer, et al., Psychol. Med 26: 1919–195, 1996). TG-2 positive cells were counted under a microscope at 200× magnification in each dish. The experiment was done in duplicate. The results are shown in FIG. 4.

Effect of Ebaf on Neuronal Markers in Rat Embryo Forebrain Cell Cultures.

Figure 5:
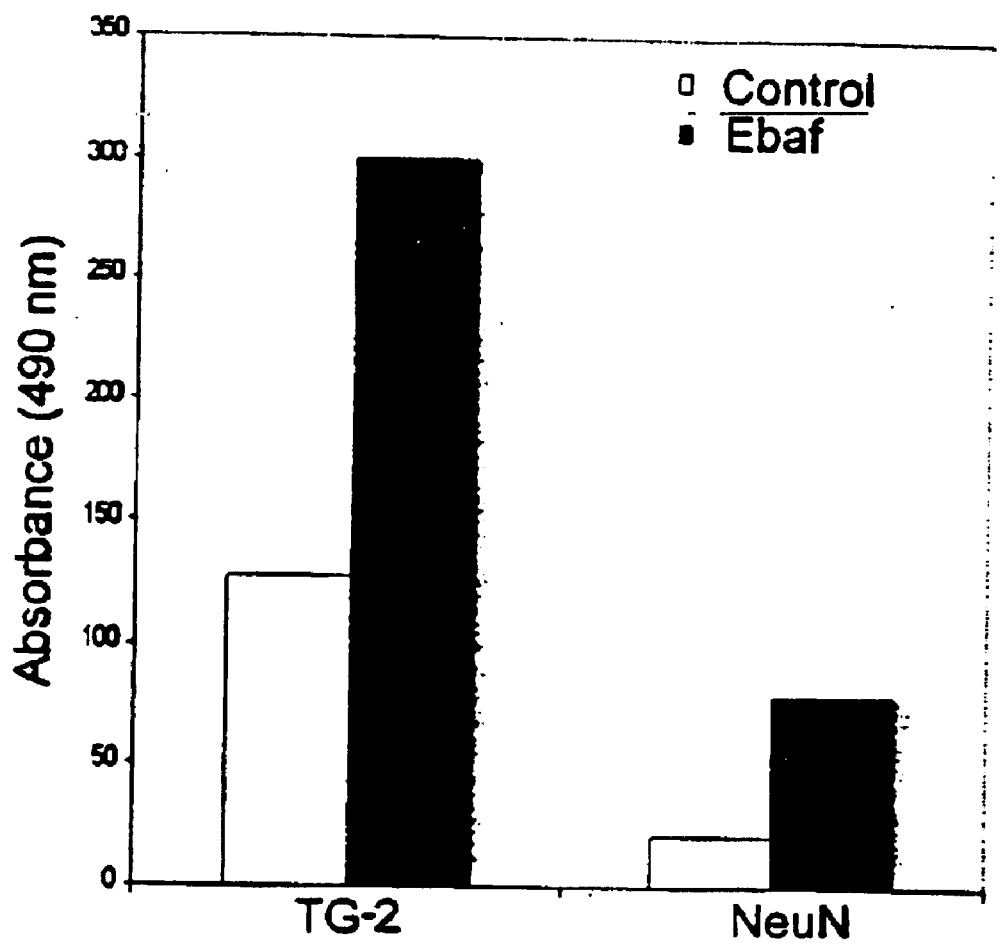
FIG. 5 depicts the effect of ebaf on neuronal number measured by ELISA. The forebrain cells were cultured as described in the text and the OD was determined for cells stained for TG-2 and NeuN2. Results shown are from the means of duplicate samples.

Cultures of dissociated, embryonic, day 16 (E16), rat forebrain were established in 24-well tissue culture plates with equal number ($250\times10^3$/well) of cells. These were maintained overnight in a chemically defined medium. The next morning, culture supernatants from confluent ebaf-transfected cells (diluted 25 fold) and DMEM medium alone were added respectively to the experimental and control wells. These were incubated for nine days in culture. Medium was replaced on day five. On day 9, the well was stained with TG-2 and NeuN antibody which both mark neuronal cells (TG-2: Honer, et al., Psychol. Med. 26: 1919–195, 1996; NeuN: Mullen, et al., Development 116: 201–211, 1992). The reaction product was produced in solution in presence of o-phenylenediamine dihydrochloride (OPD). The solutions were the transferred to a 96 well plate and the absorbance was read at 490 nm. The experiment was done in duplicate. The results are shown in FIG. 5.

All publications mentioned herein above are hereby incorporated in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for inducing proliferation of embryonic forebrain cells comprising contacting the embryonic forebrain cells in vitro with an amount of an endometrial bleeding associated factor (ebaf) protein effective to induce the proliferation of the forebrain cells, wherein the ebaf protein has the amino acid sequence set forth in SEQ ID NO:2.

2. The method of claim 1, wherein the ebaf protein is encoded by the nucleotide sequence set forth in SEQ ID NO:1.

3. A method for inducing growth or enhancing survival of forebrain cells, the method comprising contacting the forebrain cells in vitro with an amount of an endometrial bleeding associated factor (ebaf) protein effective to induce the growth or enhance the survival of the forebrain cells, wherein the ebaf protein has the amino acid sequence set forth in SEQ ID NO:2.

4. The method of claim 3, wherein the method induces cell growth.

5. The method of claim 3, wherein the method enhances cell survival.

6. The method of claim 3, wherein the method induces neuronal growth or enhances neuronal survival.

7. The method of claim 3, wherein the ebaf protein is encoded by the nucleotide sequence set forth in SEQ ID NO:1.

8. The method of claim 6, wherein the method induces neuronal growth.

9. The method of claim 8, wherein the method enhances neuronal survival.

* * * * *

SEQUENCE LISTING

<160> NUMBER OF SEQ ID NOS: 2

<210> SEQ ID NO 1
<211> LENGTH: 2012
<212> TYPE: DNA
<213> ORGANISM: homo sapiens

<400> SEQUENCE: 1

```
aattcggcac gagccccact ctgcctcctg ctcccccagg gcagcaccat gtggcccctg      60
tggctctgct gggcactctg ggtgctgccc ctggctggcc ccggggcggc cctgaccgag     120
gagcagctcc tgggcagcct gctgcggcag ctgcagctca gcgaggtgcc cgtactggac     180
agggccgaca tggagaagct ggtcatcccc gcccacgtga gggcccagta tgtagtcctg     240
ctgcggcgca gccacgggga ccgctcccgc ggaaagaggt tcagccagag cttccgagag     300
gtggccggca ggttcctggc gtcggaggcc agcacacacc tgctggtgtt cggcatggag     360
cagcggctgc cgcccaacag cgagctggtg caggccgtgc tgcggctctt ccaggagccg     420
gtccccaagg ccgcgctgca caggcacggg cggctgtccc cgcgcagcgc ccaggcccgg     480
gtgaccgtcg agtggctgcg cgtccgcgac gacggctcca accgcacctc cctcatcgac     540
tccaggctgg tgtccgtcca cgagagcggc tggaaggcct tcgacgtgac cgaggccgtg     600
aacttctggc agcagctgag ccggccccgg cagccgctgc tgctacaggt gtcggtgcag     660
agggagcatc tgggcccgct ggcgtccggc gcccacaagc tggtccgctt tgcctcgcag     720
ggggcgccag ccgggcttgg ggagcccag ctggagctgc acaccctgga cctcagggac     780
```

```
tatggagctc agggcgactg tgaccctgaa gcaccaatga ccgagggcac ccgctgctgc    840
cgccaggaga tgtacattga cctgcagggg atgaagtggg ccaagaactg ggtgctggag    900
cccccgggct tcctggctta cgagtgtgtg ggcacctgcc agcagccccc ggaggccctg    960
gccttcaatt ggccatttct ggggccgcga cagtgtatcg cctcggagac tgcctcgctg   1020
cccatgatcg tcagcatcaa ggagggaggc aggaccaggc cccaggtggt cagcctgccc   1080
aacatgaggg tgcagaagtg cagctgtgcc tcggatgggg cgctcgtgcc aaggaggctc   1140
cagccatagg cgcctggtgt atccattgag ccctctaact gaacgtgtgc atagaggtgg   1200
tcttaatgta ggtcttaact ttatacttag caagttactc catcccaatt tagtgctcct   1260
gtgtgacctt cgccctgtgt ccttccattt cctgtctttc ccgtccatca cccatcctaa   1320
gcacttacgt gagtaaataa tgcagctcag atgctgagct ctagtaggaa atgctggcat   1380
gctgattaca agatacagct gagcaatgca cacattttca gctgggagtt tctgttctct   1440
ggcaaattct tcactgagtc tggaacaata atacccctatg attagaactg gggaaacaga   1500
actgaattgc tgtgttatat gaggaattaa aaccttcaaa tctctatttc ccccaaaatac   1560 tgacccattc tggactttg taaacatacc taggcccctg ttcccctgag agggtgctaa    1620
gaggaaggat gaagggcttc aggctggggg cagtggacag ggaattggga tacctggatt   1680
ctggttctga cagggccaca agctaggatc tctaacaaac gcagaaggct ttggctcgtc   1740
atttcctctt aaaaggagg agctgggctt cagctctaag aacttcattg ccctggggat    1800
cagacagccc ctacctaccc ctgcccactc tctggagac tgagccttgc ccgtgcatat    1860
ttaggtcatt tcccacactg tcttagagaa cttgtcacca gaaaccacat gtatttgcat   1920
gttttttgtt aatttagcta aagcaattga atgtagatac tcagaagaaa taaaaaatga   1980
tgtttcaaaa aaaaaaaaaa aaaaaactcg ag                                 2012
```

<210> SEQ ID NO 2
<211> LENGTH: 366
<212> TYPE: PRT
<213> ORGANISM: homo sapiens

<400> SEQUENCE: 2

```
Met Trp Pro Leu Trp Leu Cys Trp Ala Leu Trp Val Leu Pro Leu Ala
1               5                   10                  15

Gly Pro Gly Ala Ala Leu Thr Glu Glu Gln Leu Leu Gly Ser Leu Leu
                20                  25                  30

Arg Gln Leu Gln Leu Ser Glu Val Pro Val Leu Asp Arg Ala Asp Met
            35                  40                  45

Glu Lys Leu Val Ile Pro Ala His Val Arg Ala Gln Tyr Val Val Leu
        50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Gln Ala Arg
    130                 135                 140

Val Thr Val Glu Trp Leu Arg Val Arg Asp Asp Gly Ser Asn Arg Thr
145                 150                 155                 160
```

-continued

```
Ser Leu Ile Asp Ser Arg Leu Val Ser Val His Glu Ser Gly Trp Lys
            165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
            195             200                 205

Gly Pro Leu Ala Ser Gly Ala His Lys Leu Val Arg Phe Ala Ser Gln
        210             215                 220

Gly Ala Pro Ala Gly Leu Gly Glu Pro Gln Leu Glu Leu His Thr Leu
225                 230                 235                 240

Asp Leu Arg Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Lys Asn Trp Val Leu Glu Pro Pro Gly Phe
        275                 280                 285

Leu Ala Tyr Glu Cys Val Gly Thr Cys Gln Gln Pro Pro Glu Ala Leu
        290                 295                 300

Ala Phe Asn Trp Pro Phe Leu Gly Pro Arg Gln Cys Ile Ala Ser Glu
305                 310                 315                 320

Thr Ala Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
            355                 360                 365
```